(12) United States Patent
Yoo

(10) Patent No.: US 9,504,849 B2
(45) Date of Patent: Nov. 29, 2016

(54) DESTRUCTION OF TARGET CELLS UTILIZING HARMONIC RESONANCE CAVITATION

(71) Applicant: PLUMERIA HOLDINGS, LLC, East Haven, CT (US)

(72) Inventor: Duke Sangyoung Yoo, East Haven, CT (US)

(73) Assignee: PLUMERIA HOLDINGS, LLC, East Haven, CT (US)

( * ) Notice: Subject to any disclaimer, the term of this patent is extended or adjusted under 35 U.S.C. 154(b) by 194 days.

(21) Appl. No.: 14/209,159

(22) Filed: Mar. 13, 2014

(65) Prior Publication Data

US 2014/0277295 A1 Sep. 18, 2014

Related U.S. Application Data

(60) Provisional application No. 61/785,321, filed on Mar. 14, 2013.

(51) Int. Cl.
*A61N 5/06* (2006.01)
*A61N 5/067* (2006.01)

(52) U.S. Cl.
CPC ....... *A61N 5/0624* (2013.01); *A61N 2005/067* (2013.01)

(58) Field of Classification Search
CPC ................. A61N 5/0624; A61N 5/06; A61N 2005/067; A61B 18/20; A61B 18/203; A61B 18/26; A61B 2018/205; A61B 2018/208
See application file for complete search history.

(56) References Cited

U.S. PATENT DOCUMENTS

| 8,277,495 | B2* | 10/2012 | Demetriou | A61B 18/14 128/898 |
| 2003/0181847 | A1* | 9/2003 | Bruno-Raimondi | A61K 41/00 604/20 |
| 2008/0172047 | A1* | 7/2008 | Altshuler | A61B 5/441 606/9 |
| 2011/0295343 | A1* | 12/2011 | Bornstein | A61N 5/0616 607/88 |

* cited by examiner

*Primary Examiner* — Gary Jackson
*Assistant Examiner* — Joshua Rosefelt
(74) *Attorney, Agent, or Firm* — Wiggin and Dana LLP; Gregory S. Rosenblatt

(57) ABSTRACT

A method to enable a laser to interact with a structure behind a barrier includes calculating a set of characteristics for a first laser channel to be effective to tunnel through the barrier and calculating a second set of characteristics for a second laser channel to be effective to interact with the structure, generating said first laser pulse to form a tunnel through the barrier and prior to closing of the tunnel, generating the second laser pulse to travel through the tunnel to interact with the structure. A treatment unit associated with this method has a control panel in communication with an electronics package. Data entered into the control panel enables the electronics package to calculate the first and second sets of characteristics and drive a first laser generating a laser pulse of the first laser channel followed after a delay by a laser pulse of the second laser channel.

24 Claims, 3 Drawing Sheets

DESTRUCTION OF TARGET CELLS UTILIZING HARMONIC RESONANCE CAVITATION

CROSS REFERENCE TO RELATED APPLICATION(S)

This patent application claims a benefit to the filing date of U.S. Provisional Patent Application Ser. No. 61/785,321, titled "Destruction of Target Cells Utilizing Harmonic Resonance Cavitation," that was filed on Mar. 14, 2013. The disclosure of U.S. 61/785,321 is incorporated by reference herein in its entirety.

U.S. GOVERNMENT RIGHTS

N.A.

BACKGROUND

Field

Disclosed herein is an apparatus and method to destroy specific covalent bonds or organic molecules of target cells by direct energy transfer from quantized photons, such as multiple lasers, via harmonic resonance cavitation. More particularly, the apparatus and method are useful to destroy under nail fungus.

Description of the Related Art

To date, treatments utilizing medical lasers primarily rely on heat. During treatment, the precisely quantized photon energy produced by the laser is converted into incoherent thermal energy. This thermal energy, heat, is used to destroy a target. There are a number of shortcomings with current laser heat treatments, including (1) the same heat can harm and burn normal healthy human tissue; (2) attenuation depth of the heat transfer cannot be precisely controlled due to multi-layers of different types of tissue in the human body; and (3) thermodynamics dictates that when one form or energy (laser) is transformed to another form of energy (heat via a thermo decoupling process), a significant quantity of the original energy is lost during the transformation.

Due to the losses associated with the laser, to generate heat for the thermo decoupling process, current medical lasers use multi-wattage lasers, such as from about 4 watts to over 120 watts. To place in perspective, in the metal fabrication industry, lasers with wattages of between 10 watts and 100 watts are used to cut thick steel plates.

Laser-to-heat treatments are known to kill toe nail and finger nail fungus (onychomycosis). Exemplary methods and devices are disclosed in U.S. Pat. No. 8,277,495, "Method and Apparatus for Treating a Diseased Nail," by Demetriou et al. and United States Patent Application Publication No. US 2011/0178510 A1, "Method and Device to Inactivate and Kill Cells and Organisms That Are Undesirable," by Cumbie et al. Both U.S. Pat. No. 8,277,495 and US 2011/0178510 A1 are incorporated by reference herein in their entireties.

A normal, healthy, nail plate has between about 25 and 27 layers of dehydrated human skin, keratin. Typically, nail fungi proliferate in a space between the nail plate above and the skin below (nail bed). In order to kill toe nail fungus or finger nail fungus, a medical laser must penetrate the nail plate without harming normal top nail plate layers and then break apart the fungus cell structure without burning nerve endings and skin cells located on the nail bed. Current laser-to-heat treatments are not ideal because: (1) the heat can burn normal nail plate or surrounding skin; (2) attenuation depth, also referred to as therapeutic penetration depth, of heat cannot be controlled effectively because heat loses its kill power effectiveness as different layers are encountered; (3) nail fungus located deeper than the minimum effective threshold of heat power remains untreated (failed to kill the fungus); and (4) because of inefficient conversion of laser photon quantum energy to thermo energy, current medical lasers are rated at between about 4 watts and about 80 watts to kill nail fungus.

BRIEF SUMMARY OF THE INVENTION

In accordance with a first embodiment, there is provided a method to enable a laser to interact with a structure disposed behind a barrier. This method includes the steps of calculating a set of first characteristics for a first laser channel to be effective to tunnel through the barrier and calculating a second set of characteristics for a second laser channel to be effective to interact with the structure, generating said first laser pulse to form a tunnel through the barrier and prior to closing of the tunnel, generating the second laser pulse to travel through the tunnel to interact with the structure.

In accordance with a second embodiment, there is provided a treatment unit including a laser that interacts with a structure disposed behind a barrier. The treatment unit has a control panel in communication with an electronics package. Data entered into the control panel enables the electronics package to calculate a first set of characteristics for a first laser channel to be effective to tunnel through the barrier and to calculate a second set of characteristics for a second laser pulse effective to interact with the structure. The electronics package driving the first laser generates a laser pulse of the first laser channel followed within a predetermined time delay by a laser pulse of the second laser channel.

In one application, the barrier is a finger nail or a toe nail and the structure is a fungus.

The details of one or more embodiments of the invention are set forth in the accompanying drawings and the description below. Other features, objects and advantages of the invention will be apparent from the description and drawings, and from the claims.

BRIEF DESCRIPTION OF THE DRAWINGS

Like reference numbers and designations in the various drawings indicated like elements.

DETAILED DESCRIPTION

Figure 1:
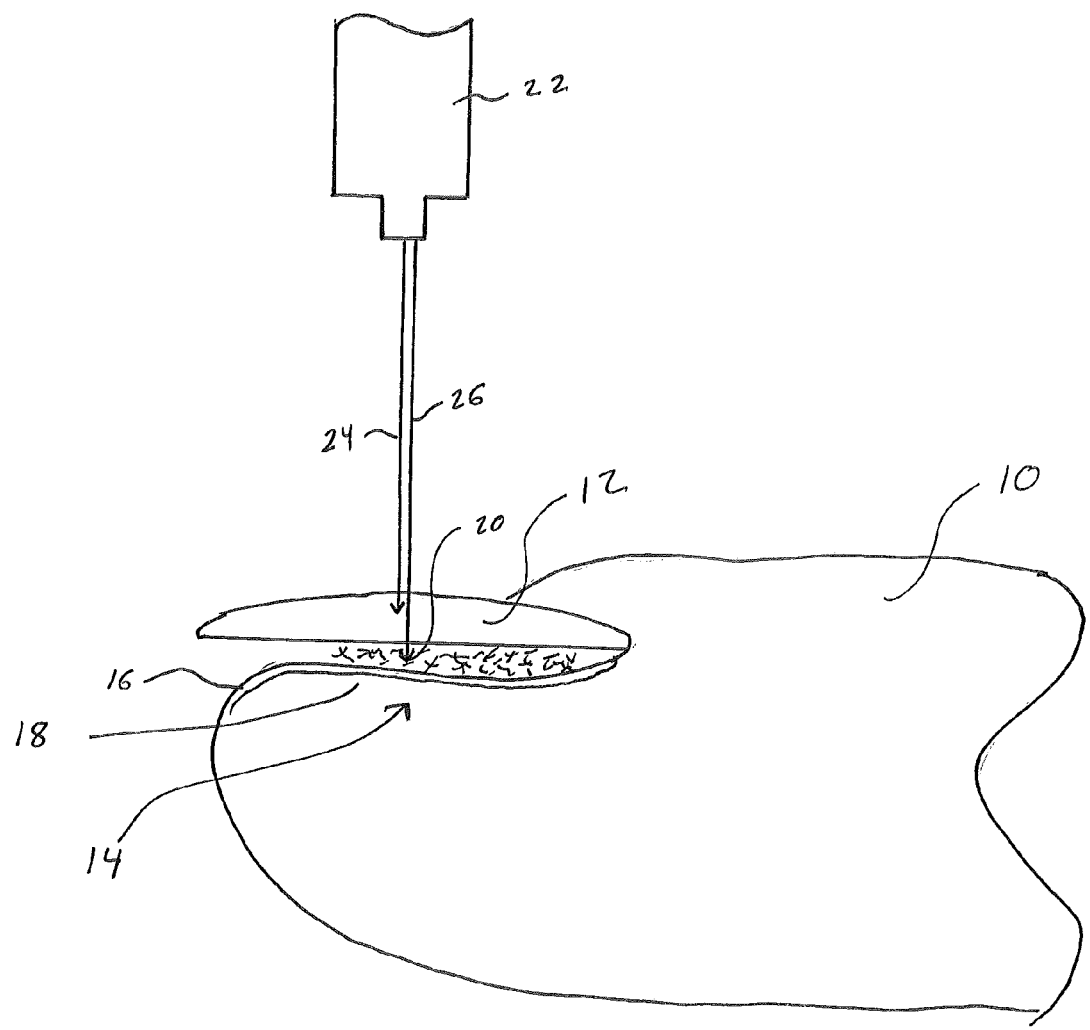
FIG. 1 illustrates an apparatus treat nail fungus utilizing harmonic resonance cavitation.

The apparatus and method utilized herein combine medicine and electrodynamics. By combining medically known clinical facts with proven biomolecular reactions in physiological and pathological states of human bodies and with also some very specific equations in quantum electrodynamics (exemplary are Schrodinger's Many Body Equations, Kohn-Sham Equation, and Density Functional Theory) and achieving numerical solutions to such equations, it is possible to calculate precise energy modulation values for therapeutic lasers for specific target molecules and atoms covalent bonds.

Controlled direct-quantized energy, such as a first set of laser beams, penetrates covalent bonds of organic molecular barriers without interacting with the barrier molecular bonds, but creates a cavity (tunneling effect through the first barrier). Then, a second set of lasers penetrates the barrier without interacting with the barrier molecules through the cavity created by the first set of lasers. This second set of lasers would have interacted with the barrier molecules, such as by a loss of laser energy, breaking molecular covalent bonds, or burning tissue, if the first set of lasers did not create the "cavity" or "tunnel" via harmonic resonance cavitations.

In medical and biological settings, the main barriers are organic molecules with covalent bonds. Due to their inherent size and geometry as well as distances between the atoms and molecules forming such complex molecular bonds, such as polypeptides, the effective range for low level laser therapy utilizing harmonic resonance cavitations for lasers is a laser with a wavelength between 0.1 nm and 5000 nm. With expected optical laser energy levels of sub milli watt to instantaneous (in pico and femto second pulses) peak laser power of over 25 watts.

The first set of lasers creates a cavity or tunnel, through which the second set of "kill" lasers can penetrate deeper into tissue layers unchanged until hitting (interacting with) the target organic molecules of target cells. This "kill" laser portion will break certain specific covalent bonds of the target molecule, and only those target cells made of the target molecules will be destroyed. Surrounding cells without "the target molecules" are "transparent" to either the first or second sets of lasers.

By directly interacting, between precisely controlled and modulated laser photon quantum energy, with the target molecule's specific organic covalent bond's electron's quantum energy levels, a minimum amount of the original laser energy is lost. Therefore, only very low amounts (in milli-watts for killing fungus or bacteria) of laser power is required to achieve breaking of the target organic molecular covalent bonds.

With harmonic resonance cavitations, it is possible to destroy nail fungus (onychomycosis) under the nail plate, without harming surrounding normal human tissues, such as nail plate, epidermis, and dermis. The first set of lasers will penetrate nail plate creating a cavity (tunneling effect). Then, the second set of lasers will penetrate the nail plate through the cavity created by the first laser set. The second laser set will have no interaction with the nail plate. This second laser set is precisely calibrated to interact with one target organic molecule of covalent bonds. For fungi that is N-Acetyl-D-Glucosamine. This N-Acetyl-D-Glucosamine is the main structural element of cell wall. Fungus and bacteria (and plants) have cell walls, whereas animals (including humans) do not.

Therefore, the second laser set will break covalent bonds of N-Acetyl-D-Glucosamine, hence breaking fungus cell wall, then the fungus ruptures and dies. Whereas, other surrounding cells that do not have N-Acetyl-D-Glucosamine, such as human nail or skin, are unaffected. All this is achieved with very low power lasers, due to harmonic resonance cavitations.

FIG. 1 illustrates a first treatment method. A toe 10 includes a nail 12 overlying a nail bed 14. Nail bed 14 includes an epidermis 16 overlying a dermis 18. Epidermis 16 includes sensitive nerve endings while dermis 18 includes both a vascular network and nerves. Disposed between the nail 12 and nail bed 14 is a fungus 20. As noted above, the nail 12 is primarily formed from keratin. A laser 22 includes at least two laser channels. A first channel 24 has a frequency, wavelength and duration effective to tunnel through nail 12.

Exemplary values for the first laser channel are:
Frequency—2 HZ-200 MHz;
Wavelength—405 nm with +/−10 nm; and
Duration—with less than 5 nano-second Gaussian Power rise time on laser diode, 0.5 second~5 nano-second.

The tunnel formed through the nail 12 by the first laser channel remains open for about 5 nano-seconds. Within that time, a pulse from a second laser channel 26 is directed through the tunnel to interact with the cell wall, N-Acetyl-D-Glucosamine, of fungus 20. The second laser channel has a frequency, wavelength and duration effective to disrupt the cell wall, thereby killing the fungus, without interacting with the underlying nail bed 14. Exemplary values for the second laser channel are:
Frequency—20 Hz-200 MHz;
Wavelength—980 nm+/−5 nm; and
Duration—with less than 5 nano-second Gaussian Power rise time on laser diode, 0.5 second~5 nano-second.

Calculating the frequency, wavelength and durations for the first and second pulses utilizes the quantum equations disclosed herein above. An exemplary set of equations follows:

Calculating the lasers frequencies, wavelengths and durations for the first and second pulses utilizing quantum equations disclosed herein above, is only a small part of finalizing and selecting correctly harmonized Laser combinations. It was further researched and verified with already published scientific data, both estimated (simulated) by computer programs, and by experimentally obtained values for electron energy level values and atomic-molecular geometry. An exemplary set of equations and published data follows:

Density Functional Theory/Kohn-Sham Equations:

$$\left(-\frac{1}{2m}\nabla^2 + V_{eff}[n(r)]\right)\psi_i(r) = E_i\psi_i(r),$$

$$n(r) = 2\sum_{i=1}^{N_E} |\psi_i(r)|^2.$$

$$V_{eff}[n(r)] = V_{ion}(r) + V_H[n(r)] + V_{XC}[n(r)],$$

$$-\nabla^2 V_H(r) = \frac{\rho(r)}{\epsilon}.$$

The density functional theory (DFT) is presently the most successful (and also the most promising) approach to compute the electronic structure of matter. Its applicability ranges from atoms, molecules and solids to nuclei and quantum and classical fluids. In its original formulation, the density functional theory provides the ground state properties of a system, and the electron density plays a key role. An example: chemistry. DFT predicts a great variety of molecular properties: molecular structures, vibrational frequencies, atomization energies, ionization energies, electric and magnetic properties, reaction paths, etc. The article, "Targeted Energy Transfer by Fermi Resonance" by Maniadis et al. is appended hereto to further describe the above equation. The article shows that complete energy transfer may also occur by harmonics resonance under a condition similar to those of targeted energy transfer (TET). This effect is called Fermi targeted energy transfer (or FTET).

Atomistic Methods when describing Interfaces, such as barriers between nail plate and nail fungus:

SMALL systems (billions of atoms are not that many)
Non-local effects (curvature, strain, magnetic, electric fields) are not easy to capture (if at all)
Continuum Descriptions of Heterogeneous Systems (i. e. with interfaces)

$$F[\phi, T, \ldots] = \int_\Omega f[\phi, T, \ldots] + \frac{k}{2}(\nabla\phi)^2 \, d\Omega$$

Free Energy is not local anymore. The Total free energy of a system now depends on heterogeneities in macroscopic properties, as shown below:

$$F[\phi, T, \ldots] = \int_\Omega f[\phi, T, \ldots] + \frac{k}{2}(\nabla\phi)^2 \, d\Omega + \frac{1}{2}\int_\Omega \vec{\sigma} \cdot \vec{\varepsilon} \, d\Omega$$

$$\sigma_{i,j} = C_{ijkl}(\varepsilon_{kl} - \beta_{kl}(\phi - \phi_o))$$

The article, "Texas Materials Modeling Network" by Srini et al. is appended hereto to further describe the above equation.

An article (appended), titled Coherent Laser Control of the Resonance-Enhanced Multiphoton Ionization of HCl" by Park et al. demonstrated how to ionize (or break certain molecular bonds by breaking that molecule's covalent electron bond): Also describes how to calculate numerical values for such Laser-Molecule interactions. The same equation can be used for other molecules, other than HCl.

$$\Psi(t) = \sum_{M'} |J', M'\rangle \exp(-iEt/\hbar) \times \langle J',$$

$$M' | \{\varepsilon_3 \exp[i(\theta_3 + k_3 \cdot z)]\hat{\varepsilon}_3 \cdot \mu - \varepsilon_1^3 \times \exp[3i(\theta_1 + k_1 \cdot z)]\}T | J'', M''\rangle$$

An article, appended, titled "Generalized Kohn-Sham Approaches" by Baer, discloses such information as phonon dispersion curves (such as Laser photon on to a target molecule), dielectric responses, and ionization potentials in 3-D electron-density contours. While an article titled "Numerical Solution of the Kohn-Sham Equation by Finite Element Methods with an Adaptive Mesh Redistribution Technique" by Bao et al. demonstrates calculating numerical values of Kohn-Sham equations Atomization energies of molecules, in eV (1 eV=23.1 kcal/mol), such molecules as $O_2$, $H_2O$, $CH_4$, $NH_3$, etc. are published, as are hydrogen bonding energy landscape: geometry for complex molecules, such as proteins and alpha-helices (organic molecules). Published all-electron numerical and computational calculations for atoms and molecules; such biological atoms and molecules as,

|  | Atoms, Molecules | | | | |
| --- | --- | --- | --- | --- | --- |
|  | C | O | $H_2$ | CO | $C_6H_6$ |
| Size of Hamiltonian matrix | ~6,000 | ~6,000 | ~8,000 | ~35,000 | ~120,000 |
| Total Energy (ev) | −1018.47 | −2026.75 | −31.24 | −3060.88 | −6263.53 |
| FHI-aims (ev) | −1018.37 | −2026.45 | −30.95 | −3060.53 | −6263.83 |

Published calculated/predicted by computer simulation/experimental geometric values of typical organic molecules, in size of 10 nm length through 1DFTB SCC-DFTB DFT-LSD methods.

|  | DFTB | SCC-DFTB | DFT-LSD | Experimental |
| --- | --- | --- | --- | --- |
| C=O | 1.296 | 1.224 | 1.223 | 1.193 |
| C—N | 1.296 | 1.382 | 1.358 | 1.376 |
| N—H | 1.003 | 0.996 | 1.022 | 1.002 |
| C—H | 1.130 | 1.131 | 1.122 | 1.102 |
| OCN | 127.0 | 125.5 | 124.5 | 123.8 |

1DFTB—Density-Functional Tight-Binding
SCC-DFTB—Self-Consistent-Charge Density-Functional Tight-Binding
DFT-LSD—Density Functional Theory - Local Spin Density Published such data as Bond lengths for different bonding situations [in Angstrom]:

| Bond | LDA | BLYP | BP86 | Experimental |
| --- | --- | --- | --- | --- |
| H—H | 0.765 | 0.748 | 0.752 | 0.741 |
| H3C—CH3 | 1.510 | 1.542 | 1.535 | 1.526 |

LDA—Local Density Approximations
BLYP (also known as B3LYP)—Becke (exchange) and Lee, Young, Palmer (correlation) density functional calculations
BP86—Becke (exchange) and Perdew (correlation) density functional calculations model-86.

Figure 2:
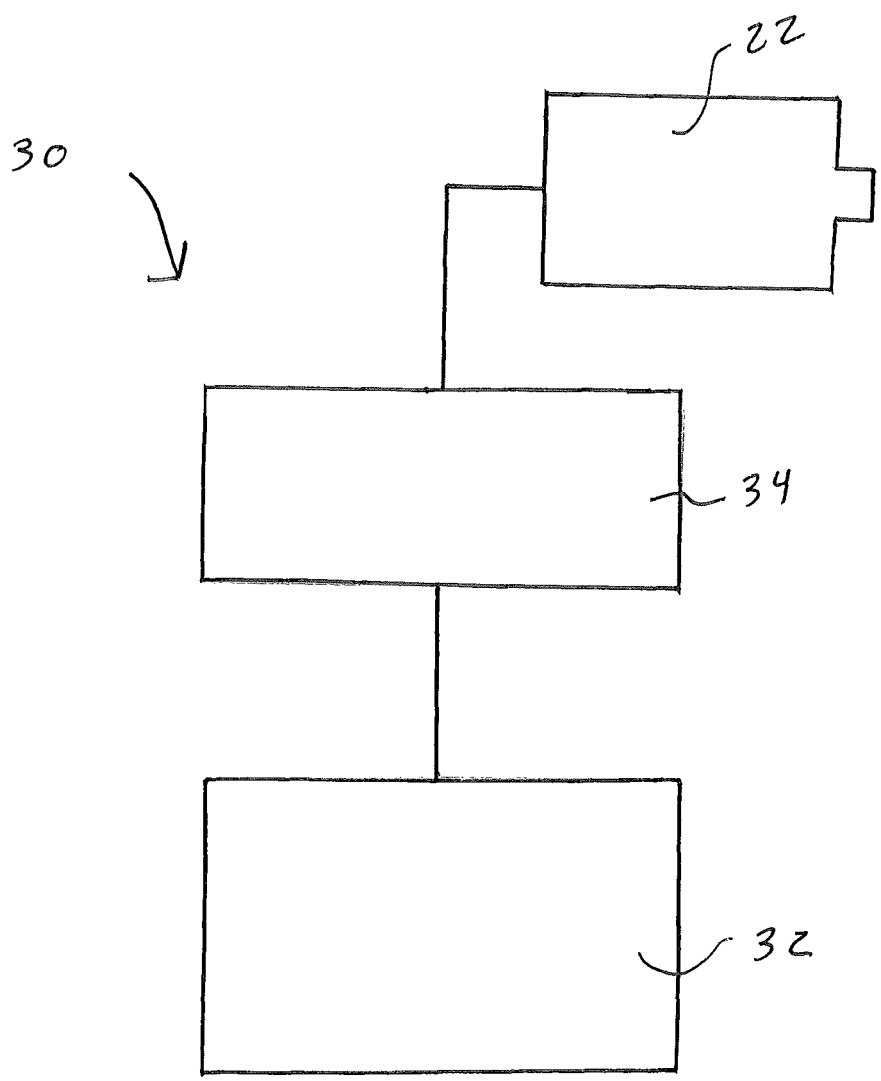
FIG. 2 is a block diagram of components forming the apparatus of FIG. 1.

FIG. 2 illustrates an exemplary apparatus 30 for use with the method described herein. The apparatus 30 includes a control panel 32 where an operator inputs data necessary to calculate required frequencies, wavelengths and durations. This data includes severity of onychomycosis (nail fungus infection); such as nail color changes, dystrophic nail thickness changes, subungual debris presence, onycholysis, secondary infection state (such as secondary bacterial infection), or presence of nail/skin psoriatic changes. Microprocessors located in an electronics package 34 then perform the necessary calculations and drive one or more lasers 22 with the proper frequency modulation and power modulation for the first and second laser channels. Multiple lasers may be employed for the multiple channels.

Figure 3:
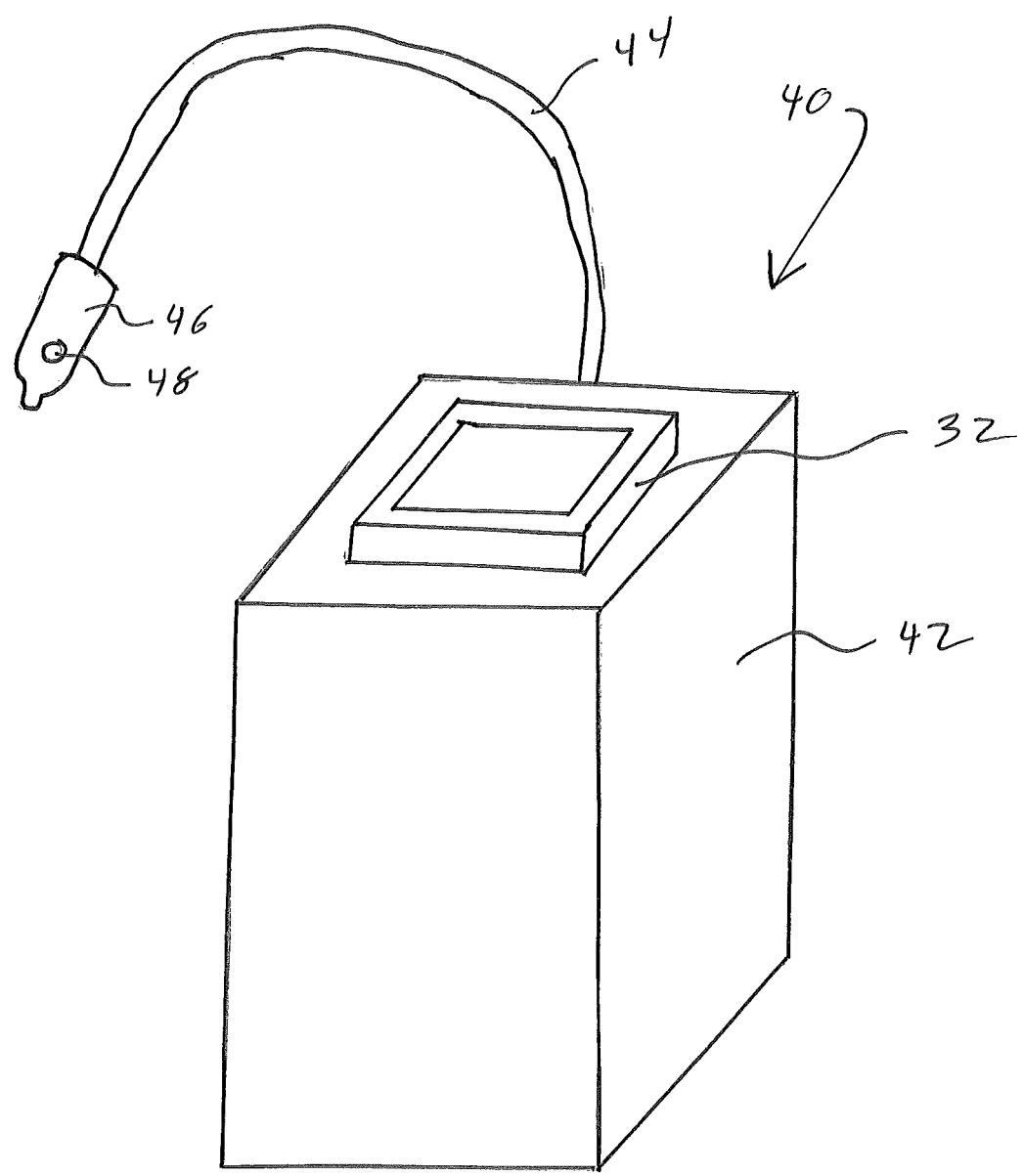
FIG. 3 illustrate one embodiment of the apparatus of FIG. 1.

A compact unit 40 such as for use in a doctor's office, hospital or clinic, is illustrated in FIG. 3. Housing 42 includes a power unit, microprocessors, lasers and cooling elements. The housing may be on wheels (not shown) to enhance portability. A control panel 32 interfaces with the electronics package contained within the housing 42. The interface may be by a wire or wireless and utilizes any effective communication system. In one embodiment, the control panel 32 is a digital tablet having touch screen control panel and wireless communication capabilities. A fiber optic cable 44 directs the laser beams (first laser channel and second laser channel) to a target. The fiber optic cable 44 terminates at a laser beam terminal 46 that may be a hand piece with an on/off finger switch 48. Treatment includes the operator entering data necessary to calculate values required for the first laser channel and for the second laser channel into the control panel. Microprocessors than calculate the values. The operator then positions the laser beam terminal 46 over an infected nail and presses the finger switch 48 causing a tunneling first laser channel pulse followed by a disrupting (fungal killing) second laser channel pulse to be emitted.

A feature of the apparatus and method described herein is harmonic resonance cavitations, penetration of barriers without interaction, so that the deeper target structures can be manipulated or treated with minimum required energy, without negative side effects, such as burning, to non-target organic or inorganic molecules, cells, tissues and/or organs. While described above for destruction of a nail fungus, many other applications are envisioned.

With harmonic resonance cavitation, it is possible to excite or denature (destroy) telomere portions of human DNA inside a cell nucleus. Final treatment portion of lasers will penetrate cell membrane, cytoplasm, nucleus membrane (all without interacting with these barrier structures): then, treat only the telomere portion of certain target DNA.

One alternative for such treatment method is gene therapy. Current gene therapy relies on direct chemical reactions, such as enzymatic reactions, between drugs and target molecules of the cell. Other applications include, but are not limited to, fungus killing lasers, bacteria killing lasers, skin cancer treatment lasers, intra-articular and extra-articular joint treatment lasers, stem cell excitation lasers, cardiac ablation lasers, GI, GU, Pulmonary and OB/GYN ablation lasers, neurological lasers, vascular lasers, analgesic lasers, hair removal lasers, hair growth lasers, tattoo removal lasers, ulcer and wound care lasers, fibroblast and growth factor stimulating lasers, dental lasers and ophthalmic lasers.

Example

Following Phase I with initial testing of treated and not treated plates showing growth, then finding the tested areas marked with Gentian Violet showing no growth, Phase II was initiated. It should also be noted that Phase I was done utilizing the initial prototype which did not have the alignment of the two sets of lasers in sync at the focal point properly.

Test I Agar plates

| Sample Number | Plate Without Treatment | Plate With Laser Treatment | Plate With Sample that Had Color and Laser Treated |
|---|---|---|---|
| I | Abundant Growth | Increased Growth | Minimal (<5%) Growth |
| II | No Growth | No Growth | No Growth |
| III | Abundant Growth | Abundant Growth | No Growth |

Test II DTM (Dermatophyte Test Medium)

| Sample Number | DTM Without Treatment | DTM With Laser Treatment | DTM With Sample that Had Color and Laser Treated |
|---|---|---|---|
| I | Growth | Growth | No Growth |
| II | Growth | No Growth | No Growth |
| III | No Growth | No Growth | No Growth |
| IV | Growth | Growth | No Growth |

Test III Plates colored and targeted

| Sample Number | Portion Without Treatment | Portion With Laser Treatment | Portion With Sample that Had Color and Laser Treated |
|---|---|---|---|
| I | Abundant Growth | Abundant Growth | No Growth |
| II | Abundant Growth | Abundant Growth | No Growth |

Test IV Partial In-Vivo tests were performed

| Sample Number | Plate Without Treatment | Plate With Color and Laser Treatment |
|---|---|---|
| I | Growth | No Growth |
| II | Growth | No Growth |
| III | Growth | Limited Growth |

This is the initial findings and results demonstrating effectiveness of the laser treatment in vitro testing. Results showed that fungal infection specimen were split into treated and not treated subparts. Those parts were then inoculated onto and grown on agar growth plates. A high percentage of those specimen that were not laser treated, grew fungal species. And when the same specimen was treated prior to inoculation and then grown on the same culture media, a high percentage demonstrated no growth, or translating to effective death of the fungal species. The introduction of the coloring allowed greater penetration and absorption of the Laser therapy.

One or more embodiments of the present invention have been described. Nevertheless, it will be understood that various modifications may be made without departing from the spirit and scope of the invention. Accordingly, other embodiments are within the scope of the following claims.

What is claimed is:

1. A method for enabling a laser to interact with a structure disposed behind a barrier, the structure containing a first organic molecule and the barrier containing a second organic molecule, comprising the steps of:
   providing a control panel;
   providing an electronics package having microprocessors located therein;
   communicating data about said structure and said barrier to said electronics package by way of said control panel;
   calculating by way of said microprocessors utilizing said data a set of first characteristics for a first laser pulse to tunnel through said barrier and calculating by way of said microprocessors utilizing said data a second set of characteristics for a second laser pulse, having power in the milliwatt range, to interact with said structure;
   applying said first laser pulse to said barrier forming a tunnel through said barrier, said tunnel remaining open for about 5 nano-seconds and then closing; and
   applying said second laser pulse through said open tunnel to said structure and breaking covalent bonds of said first organic molecule.

2. The method of claim 1 wherein the second organic molecule contains covalent bands that are reversibly distorted, but not broken, by the first laser pulse.

3. The method of claim 2 wherein the barrier is keratin.

4. The method of claim 3 wherein said barrier is selected to be a toe nail or finger nail and said structure is a fungus.

5. The method of claim 2 wherein said tunnel is formed by harmonic resonance cavitation wherein said first laser penetrates, without interacting with, barrier molecules thereby temporarily and reversibly forming said tunnel.

6. The method of claim 5 wherein said first laser pulse is generated by a set of first lasers and said second laser pulse is generated by a set of second lasers.

7. The method of claim 6 wherein said first set of lasers are selected to have a frequency of from 2 Hz to 200 MHz and a wavelength of from 395 nm to 415 nm.

8. The method of claim 7 wherein both said first pulse and said second pulse independently have a duration of between 5 nanoseconds and 0.5 seconds.

9. The method of claim 5 including the step of calculating characteristics of said first laser effective for harmonic resonance cavitation through said barrier wherein said first laser penetrates, without interacting with, barrier molecules thereby temporarily and reversibly forming said tunnel.

10. The method of claim 9 including the step of calculating characteristics of said second laser effective for interacting with said structure.

11. The method of claim 10 including selecting said barrier to be a toe nail or a finger nail and said structure to be a fungus whereby said interaction is rupture of a cell wall of said fungus.

12. The method of claim 11 including providing a fiber optic cable that directs the laser beams over an infected portion of the toe nail or finger nail.

13. A treatment unit including a laser that interacts with a biologic structure having covalent bonds disposed behind a biologic barrier, comprising:
   a control panel in communication with an electronics package having microprocessors located therein; wherein data entered into said control panel enables said electronics package to calculate a first set of characteristics for a first laser channel to form a tunnel through said biologic barrier and said tunnel remaining open for about 5 nanoseconds and then closing, and to calculate a second set of characteristics for a second laser pulse having power in the milliwatt range that interacts with said covalent bonds of said biologic; and
   said electronics package driving a first laser to generate a first pulse of said first laser channel followed within a predetermined time delay by the second laser pulse.

14. The treatment unit of claim 13 wherein said first laser pulse is driven by a first set of lasers and said second laser pulse is driven by a second set of lasers.

15. The treatment unit of claim 14 wherein the first laser channel has a wavelength of between 395 nm and 415 nm and the second laser channel has a wavelength of between 975 nm and 985 nm.

16. The treatment unit of claim 15 wherein the electronics package is effective to set the first laser pulse to a duration of between 5 nano-second and 0.5 second and the second laser pulse to a duration of between 5 nanosecond and 0.5 second.

17. A therapeutic treatment to kill fungus disposed under a molecular structure in human cells forming a keratin-base nail, comprising the steps of:
   providing a control panel;
   providing an electronics package having microprocessors located therein;
   communicating data about said fungus and said nail to said electronics package by way of said control panel;
   providing a first laser having first characteristics effective to tunnel through said nail, wherein said first characteristics are calculated by said microprocessors utilizing said data;
   providing a second laser having second characteristics effective to interact with said fungus, wherein said second characteristics are calculated by said microprocessors utilizing said data;
   applying a first laser pulse to said nail forming a tunnel through said nail, said tunnel remaining open for about 5 nano-seconds and then closing; and
   applying a second laser pulse through said open tunnel to interact with said fungus and break covalent bonds of molecules making up said fungus to thereby kill the fungus.

18. The therapeutic treatment of claim 17 wherein said tunnel is formed by harmonic resonance cavitation wherein said first laser distorts, without breaking, covalent bonds of said molecular structure in human cells thereby temporarily and reversibly forming said tunnel.

19. The therapeutic treatment of claim 18 wherein said first laser pulse is generated by set of first lasers and said second laser pulse is generated by a second set of lasers.

20. The therapeutic treatment of claim 19 wherein said first set of lasers are selected to have a frequency of from 2 Hz to 200 MHz and a wavelength of from 395 nm to 415 nm.

21. The therapeutic treatment of claim 20 wherein both said first pulse and said second pulse independently have a duration of between 5 nanoseconds and 0.5 seconds.

22. The therapeutic treatment of claim 18 including the step of calculating characteristics of said first laser effective for harmonic resonance cavitation through said nail wherein said first laser penetrates, without interacting with, nail molecules thereby temporarily and reversibly forming said tunnel.

23. The therapeutic treatment of claim 22 including the step of calculating characteristics of said second laser effective to rupture a cell wall of said fungus.

24. The therapeutic treatment of claim 23 wherein said cell wall of said fungus is comprised of a molecular structure N-Acetyl-D-Glucosamine.

* * * * *